United States Patent
McInally et al.

(10) Patent No.: US 6,303,613 B1
(45) Date of Patent: Oct. 16, 2001

(54) AMINOPYRIMIDINE DERIVATIVES, PROCESSES FOR THEIR PREPARATION, COMPOSITIONS CONTAINING THEM AND THEIR USE AS PHARMACEUTICALS

(75) Inventors: Thomas McInally; Alan Tinker, both of Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/101,165

(22) PCT Filed: Apr. 7, 1998

(86) PCT No.: PCT/SE98/00641

§ 371 Date: Aug. 19, 1999

§ 102(e) Date: Aug. 19, 1999

(87) PCT Pub. No.: WO98/45294

PCT Pub. Date: Oct. 15, 1998

(30) Foreign Application Priority Data

Apr. 9, 1997 (SE) .................................................. 9701304

(51) Int. Cl.[7] .......................... A61K 31/519; A61P 29/00; C07D 239/70
(52) U.S. Cl. ............................ 514/258; 544/231; 544/278
(58) Field of Search ................................ 544/231, 278; 514/258

(56) References Cited

U.S. PATENT DOCUMENTS 3,403,152  9/1968  Blatter .................................. 544/231
3,483,205  12/1969  Carney .................................. 544/231
6,046,191 * 4/2000  Hamley et al. ..................... 514/232.8

* cited by examiner

*Primary Examiner*—Richard L. Raymond
*Assistant Examiner*—Venkateraman Balasubramanian
(74) *Attorney, Agent, or Firm*—Nixon & Vanderhye

(57) ABSTRACT

There are provided novel compounds of formula (I)

(I)

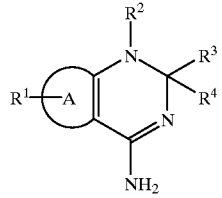

wherein:
A represents a five membered heterocyclic aromatic ring containing 1 to 3 heteroatoms which may be the same or different and are selected from O, N and S; or a six membered heterocyclic aromatic ring containing 1 to 3 nitrogen atoms; and $R^1$, $R^2$, $R^3$ and $R^4$ are as defined in the Specification and pharmaceutically acceptable salts thereof and enantiomers and tautomers thereof; together with processes for their preparation, compositions containing them and their use in therapy. The compounds are inhibitors of nitric oxide synthase and are thereby particularly useful in the treatment or prophylaxis of inflammatory disease and pain.

13 Claims, No Drawings

AMINOPYRIMIDINE DERIVATIVES, PROCESSES FOR THEIR PREPARATION, COMPOSITIONS CONTAINING THEM AND THEIR USE AS PHARMACEUTICALS

FIELD OF THE INVENTION

The present invention relates to novel compounds which are aminopyrimidine derivatives. The invention also concerns related aspects including processes for the preparation of the compounds, compositions containing them and their use as pharmaceuticals. There are also provided chemical intermediates useful for the production of the compounds.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been particularly implicated in the pathogenesis of inflammatory diseases. Regulation of these enzymes should therefore offer considerable potential in the treatment of a wide variety of disease states (J. E. Macdonald, Ann. Rep. Med. Chem., 1996, 31, 221–230).

DISCLOSURE OF THE INVENTION

According to the invention, there is provided a compound of formula (I):

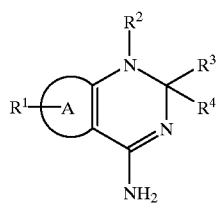

(I)

wherein
- $R^1$ represents hydrogen, alkyl C1 to 6, alkoxy C1 to 6, halogen or trifluoromethyl;
- $R^2$ represents hydrogen or alkyl C1 to 6;
- A represents a five membered heterocyclic aromatic ring containing 1 to 3 heteroatoms which may be the same or different and are selected from O, N and S; or a six membered heterocyclic aromatic ring containing 1 to 3 nitrogen atoms;
  - (i) $R^3$ represents phenyl, a six membered heterocyclic aromatic ring containing 1 to 3 nitrogen atoms, or a five membered heterocyclic aromatic ring containing 1 to 3 heteroatoms which may be the same or different and are selected from O, N and S, which phenyl or heterocyclic aromatic ring may be optionally substituted by alkyl C1 to 6, alkenyl C2 to 6, alkynyl C2 to 6, alkoxy C1 to 6, halogen, hydroxy, alkylthio C1 to 6, cyano, trifluoromethyl, nitro or a group —$NR^5R^6$;
  - and $R^4$, $R^5$ and $R^6$ independently represent hydrogen or alkyl C1 to 6; or
  - (ii) $R^3$ represents alkyl C1 to 8, alkenyl C2 to 8 or alkynyl C2 to 8;
  - and $R^4$ represents hydrogen or alkyl C1 to 6; or
  - (iii) $R^3$ and $R^4$ together represent $(CH_2)_a.Z.(CH_2)_b$, Z representing $N(COOR^7)$, wherein $R^7$ represents alkyl C1 to 6 or haloalkyl C1 to 6, or $R^7$ represents a group $(CH_2)_nYR^9$ wherein n represents an integer from 2 to 5, Y represents O, S or a bond and $R^9$ represents alkyl C1 to 6 optionally substituted by halogen or nitro, or $R^9$ represents phenyl optionally substituted by alkyl C1 to 6, halogen or nitro; and a and b independently represent an integer 1 to 3, provided that a+b is 3 or 4; or
  - (iv) $R^3$ and $R^4$ together represent $(CH_2)_a.Z.(CH_2)_b$, Z representing $N(COR^8)$, wherein $R^8$ represents phenyl, a six membered heterocyclic aromatic ring containing 1 to 3 nitrogen atoms or a five membered heterocyclic aromatic ring containing 1 to 3 heteroatoms which may be the same or different and are selected from O, N and S, which phenyl or heterocyclic aromatic ring may be optionally substituted by alkyl C1 to 6, alkoxy C1 to 6, halogen, nitro, cyano, trifluoromethyl, alkylsulphonyl C1 to 6 or aminosulphonyl; and a and b independently represent an integer 1 to 3, provided that a+b is 3 or 4, or pharmaceutically acceptable salts, enantiomers, racemates and tautomers thereof.

The invention further provides a process for the preparation of such compounds or a pharmaceutically acceptable salt, enantiomer, racemate or tautomer thereof.

According to the invention there is also provided a compound of formula (I), or a pharmaceutically acceptable salt, enantiomer, racemate or tautomer thereof, for use as a medicament.

Another aspect of the invention provides the use of a compound of formula (I) or a pharmaceutically acceptable salt, enantiomer, racemate or tautomer thereof, in the manufacture of a medicament, for the treatment or prophylaxis of diseases or conditions in which inhibition of nitric oxide synthase activity is beneficial.

A more particular aspect of the invention provides the use of a compound of formula (I) or a pharmaceutically acceptable salt, enantiomer, racemate or tautomer thereof, in the manufacture of a medicament, for the treatment or prophylaxis of inflammatory disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt, enantiomer, racemate or tautomer thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt, enantiomer, racemate or tautomer thereof.

The compounds of the present invention may also be used advantageously in combination with a second pharmaceutically active substance, particularly in combination with a selective inhibitor of the inducible isoform of cyclooxygenase (COX-2). Thus, in a further aspect of the invention there is provided the use of a compound of formula (I) or a pharmaceutically acceptable salt, enantiomer, racemate or tautomer thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt, enantiomer, racemate or tautomer thereof in combination with a COX-2 inhibitor.

Preferably, A represents a thieno ring. Especially preferred embodiments are where the compound of formula (I) is a thieno[2,3-d]pyrimidine or a thieno[3,2-d]pyrimidine.

In another preferred embodiment, A represents a pyrido ring. Especially preferred embodiments are where the compound of formula (I) is a pyrido[2,3-d]pyrimidine, pyrido[3,2-d]pyrimidine, pyrido[3,4-d]pyrimidine or pyrido[4,3-d]pyrimidine. Pyrido[3,2-d]pyrimidine compounds of formula (I) are the most preferred.

Preferably, $R^3$ represents phenyl, cyclopropyl, ethyl, thiazolyl, ethynyl or furanyl.

In another preferred embodiment, wherein $R^3$ and $R^4$ are in accordance with option (iii) in formula (I), Z represents $N(COOC_2H_5)$, and a and b each has a value of 2.

Especially preferred compounds of the invention include:

7-amino-4,5-dihydro-5-phenylthieno[3,2-d]pyrimidine;

5-cyclopropyl-4,5-dihydro-7-aminothieno[3,2-d]pyrimidine;

5-ethyl-4,5-dihydro-7-aminothieno[3,2-d]pyrimidine;

5-(2-thiazolyl)-4,5-dihydro-7-aminothieno[3,2-d]pyrimidine;

5-(2-furyl)-4,5-dihydro-7-aminothieno[3,2-d]pyrimidine;

7-amino-4,5-dihydro-5-ethynylthieno[3,2-d]pyrimidine;

ethyl 7'-aminospiro[piperidine-4,5'(4'H)-thieno[3,2-d]pyrimidine]-1-carboxylate;

ethyl 4'-amino-3'-chlorospiro[piperidine-4,6'(7'H)-thieno[2,3-d]pyrimidine]-1-carboxylate;

4'-amino-(4-cyanobenzoyl)-spiro[piperidine-4,2'-(1'H)-(pyrido[3,2-d]pyrimidine)];

4'-amino-(2-thienoyl)-spiro[piperidine-4,2'-(1'H)-(pyrido[3,2-d]pyrimidine)];

ethyl 4'-aminospiro[piperidine-4,2'-(1'H)-(pyrido[3,2-d]pyrimidine)]-1-carboxylate;

4'-amino-(4-cyanobenzoyl)-spiro[piperidine-4,2'-(1'H)-(pyrido[3,4-d]pyrimidine)];

ethyl 4'-aminospiro[piperidine-4,2'-(1'H)-(pyrido[3,4-d]pyrimidine)]-1-carboxylate;

4'-amino-(4-cyanobenzoyl)-spiro[piperidine-4,2'-(1'H)-(pyrido[4,3-d]pyrimidine)];

ethyl 4'-aminospiro[piperidine-4,2'-(1'H)-(pyrido[2,3-d]pyrimidine)]-1-carboxylate;

4-amino-2-(2-thienyl)-pyrido[3,2-d]pyrimidine;

7'-amino-1-(6-cyano-3-pyridinecarbonyl)-spiro[piperidine-4,5'-(4'H)-(thieno[3,2-d]-pyrimidine)];

and pharmaceutically acceptable salts, enantiomers or tautomers thereof.

Unless otherwise indicated, the term "C1 to 6 alkyl" referred to herein denotes a straight or branched chain alkyl group having from 1 to 6 carbon atoms or a cyclic alkyl group having from 3 to 6 carbon atoms. Examples of such groups include methyl, ethyl, n-propyl, i-propyl, n-butyl, i-butyl, t-butyl, cyclopentyl and cyclohexyl.

Unless otherwise indicated, the term "C2 to 6 alkenyl" referred to herein denotes a straight or branched chain alkyl group having from 2 to 6 carbon atoms and including one double bond or a cyclic alkyl group having from 3 to 6 carbon atoms and including one double bond. Examples of such groups include ethenyl, 1- and 2-propenyl, 2-methyl-2-propenyl, 2-butenyl, cyclopentenyl and cyclohexenyl.

Unless otherwise indicated, the term "C2 to 6 alkynyl" referred to herein denotes a straight or branched chain alkyl group having from 2 to 6 carbon atoms and including one triple bond. Examples of such groups include ethynyl, 1- and 2-propynyl and 2-butynyl.

Unless otherwise indicated, the term "C1 to 6 alkoxy" referred to herein denotes a straight or branched chain alkoxy group having from 1 to 6 carbon atoms. Examples of such groups include methoxy, ethoxy, n-propoxy, i-propoxy, n-butoxy, i-butoxy, s-butoxy and t-butoxy.

Other groups, for example, alkylthio, haloalkyl, alkylsulphonyl, are to be interpreted similarly.

The process mentioned above, for the preparation of compounds of the invention, or a pharmaceutically acceptable salt, enantiomer, racemate or tautomer thereof comprises:

(a) reaction of a compound of formula (II)

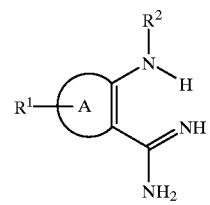

(II)

wherein A, $R^1$ and $R^2$ are as defined above, with a compound of formula (III) or an acetal derivative thereof $$R^3 \text{ C O } R^4 \quad \text{(III)}$$

wherein $R^3$ and $R^4$ are as defined above; or (b) reaction of a compound of formula (IV) or (IV')

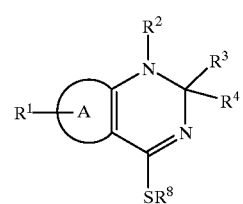

(IV)

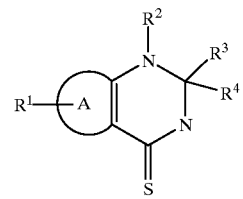

(IV')

wherein A, $R^1$, $R^2$, $R^3$ and $R^4$ are as defined above, and $R^8$ represents an alkyl group; with ammonia or an equivalent thereof; or (c) preparation of a compound of formula (I) in which $R^3$ and $R^4$ are according to option (i) in the general definition of formula (I) given above and one or both of $R^5$ and $R^6$ represents alkyl C1 to 6, by alkylation of a corresponding compound in which one or both of $R^5$ or $R^6$ represents hydrogen; or (d) preparation of a compound of formula (I) in which $R^2$ represents alkyl C1 to 6, by alkylation of a corresponding compound in which $R^2$ represents hydrogen; or (e) deprotection of a compound of formula (I) in which one or more nitrogen atoms and/or another atom is protected; or (f) preparation of a compound of formula (I) in which $R^3$ and $R^4$ are in accordance with option (iv) in the general definition of formula (I) given above, by reacting a compound of formula (V)

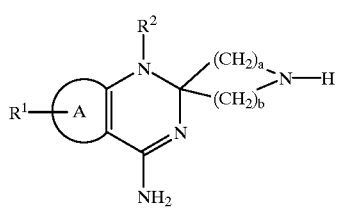

(V)

wherein A, $R^1$, $R^2$, a and b are as defined above, with a compound of formula (VI)

X—L (VI)

wherein X represents $COOR^7$ or $COR^8$, $R^7$ and $R^8$ being as above, and L is a leaving group;

and where desired or necessary converting the resultant compound of formula (I), or another salt thereof, into a pharmaceutically acceptable salt thereof, or vice versa, and where desired converting the resultant compound of formula (I) into an optical isomer thereof.

In process (a), the reaction of compounds of formulae (II) and (III) may be performed by stirring the reactants in an inert solvent at a temperature between room temperature and the boiling temperature of the solvent for a period of up to 72 hours, or until reaction is complete. We have found that it is often convenient to use the compounds of formula (III) in a protected form, for example as an acetal such as the diethoxy acetal. The process is then preferably carried out in the presence of an acid catalyst. The required acetals may be formed by reacting an unprotected compound of formula (III) with an alcohol such as ethanol using methods that are well known in the art.

In process (b), the reaction may be performed by bubbling ammonia gas through a solution of the compound of formula (IV) or (IV') in an inert polar solvent. Alternatively, the reaction may be performed by treating a solution of the compound of formula (IV) or (IV') in a polar protic solvent with aqueous ammonia, ammonia in acetonitrile or with methanolic ammonia or by treating the compound of formula (IV) or (IV') with ammonium iodide and ammonia in alcohol solution.

In processes (c) and (d), the alkylation reaction may be performed by processes well known in the art. For example, the amine may be reacted with an alkyl halide, especially an alkyl bromide or iodide.

In process (e), protecting groups for amines include alkyl, aralkyl, acyl, acyl sulphonyl, aryl sulphonyl and trialkylsilyl. Terminal alkynes may also be protected using a trialkylsilyl group. When the protecting group is trialkylsilyl, this group may be removed using, for example, tetra-n-butylammonium fluoride. Other protecting groups and further details of processes for their removal may be found by reference to the standard text "Protecting Groups in Organic Synthesis", 2nd Edition (1991) by Greene and Wuts.

In process (f), the reaction may be performed by combining the reactants in an inert solvent at a suitable temperature in the presence of a base, for example, pyridine. Although a number of standard leaving groups L are suitable, we prefer that L represents a halogen, especially chlorine or bromine.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or tautomer thereof, with one or more equivalents of the appropriate acid. The reaction may be carried out in a solvent or medium in which the salt is insoluble or in a solvent in which the salt is soluble, for example water, dioxane, ethanol, tetrahydrofuran or diethyl ether, or a mixture of solvents, which may be removed in vacuo or by freeze drying. The reaction may also be a metathetical process or it may be carried out on an ion exchange resin.

Novel intermediates of formulae (II), (IV), (IV') and (V) form another aspect of the invention. Compounds of formula (II) may be prepared by reduction of a compound of formula (VII)

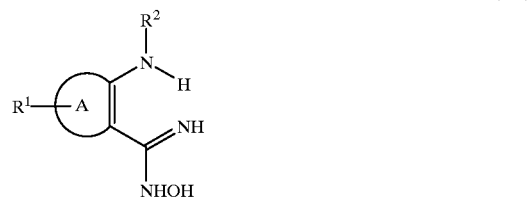

(VII)

wherein A, $R^1$ and $R^2$ are as defined above.

This reduction process may be performed by treating the compound of formula (VII) with hydrogen in the presence of palladium on carbon or rhodium on alumina or Raney nickel at elevated temperature and pressure, typically 65° C. and 30 atmospheres pressure. Compounds of formula (VII) may be prepared by reaction of a compound of formula (VIII)

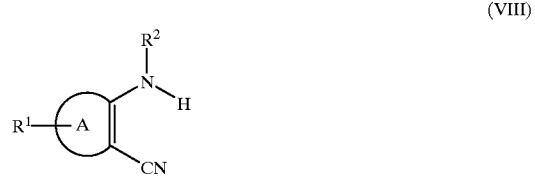

(VIII)

wherein A, $R^1$ and $R^2$ are as defined above, with hydroxylamine hydrochloride.

In this reaction, the two reactants may be heated together in the presence of a base, such as sodium methoxide, in methanol.

As alternative preparation methods for compounds of formula (II), a compound of formula (VIII) may be treated with a primary alcohol such as ethanol in the presence of acid, and subsequently treated with ammonium chloride to yield the compound of formula (II). Or a compound of formula (VIII) may be treated with a mixture of trimethylaluminium and ammonium chloride in a solvent such as toluene.

As a further alternative preparation method for compounds of formula (II), a compound of formula (IX)

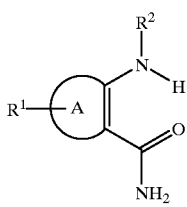

(IX)

wherein A, $R^1$ and $R^2$ are as defined above, may be treated with ammonia.

The reaction will take place under standard conditions, although a preactivation step is normally necessary, for example using Meerwein's reagent.

Compounds of formula (III), (VIII) and (IX) are either known or may be made by conventional methods known per se.

Compounds of formula (VIII) and (IX) in which $R^2$ represents alkyl C1 to 6 may be prepared by alkylation of a corresponding compound of formula (VIII) or (IX) in which $R^2$ represents hydrogen following process (d) above.

Compounds of formula (IV) may be prepared by reacting a compound of formula (X)

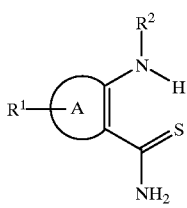

(X)

wherein A, $R^1$ and $R^2$ are as defined above, with a compound of formula (III) in the presence of an alkyl iodide.

The conditions for this reaction will be similar to those described above for process (a).

Compounds of formula (X) may be prepared by treating a compound of formula (IX) with Lawesson's reagent.

Compounds of formula (II) may also be prepared by converting a compound of formula (X) into the corresponding alkylthio derivative by treatment with an alkyl halide (especially an alkyl iodide) and subsequently reacting with ammonia following a process analogous to that of process (b) above.

Intermediate compounds may be used in protected form. Protecting groups and details of processes for their removal may be found by reference to the standard text "Protecting Groups in Organic Synthesis", 2nd Edition (1991) by Greene and Wuts.

The compounds of the invention and intermediates thereto may be isolated from their reaction mixtures and, if necessary further purified, by using standard techniques.

The compounds of formula (I) may exist in enantiomeric forms. Therefore, all enantiomers, diastereomers, racemates and mixtures thereof are included within the scope of the invention.

The various optical isomers may be isolated by separation of a racemic mixture of the compounds using conventional techniques, for example fractional crystallisation or HPLC.

Intermediate compounds may also exist in enantiomeric forms and may be used as purified enantiomers, diastereomers, racemates or mixtures thereof.

The compounds of formula (I) may exist in alternative tautomeric forms. Compounds of formula (I) are provided in another tautomeric form or as a mixture thereof.

The compounds of formula (I), and their pharmaceutically acceptable salts, enantiomers, racemates and tautomers, are useful because they possess pharmacological activity in animals. In particular, the compounds are active as inhibitors of the enzyme nitric oxide synthase. More particularly, they are inhibitors of the inducible isoform of the enzyme nitric oxide synthase present in macrophages and as such are predicted to be useful in therapy, for example, as anti-inflammatory agents.

The compounds and their pharmaceutically acceptable salts, enantiomers, racemates and tautomers are indicated for use in the treatment or prophylaxis of diseases or conditions in which synthesis or oversynthesis of nitric oxide synthase forms a contributory part. In particular, the compounds are indicated for use in the treatment of inflammatory conditions in mammals, including man.

Conditions that may be specifically mentioned are:

osteoarthritis, rheumatoid arthritis, rheumatoid spondylitis, gouty arthritis and other arthritic conditions, inflamed joints;

eczema, psoriasis, dermatitis or other inflammatory skin conditions such as sunburn;

inflammatory eye conditions including uveitis and conjunctivitis;

lung disorders in which inflammation is involved, for example, asthma, bronchitis, pigeon fancier's disease, farmer's lung, acute respiratory distress syndrome;

bacteraemia, endotoxaemia (septic shock), aphthous ulcers, gingivitis, pyresis, pain and pancreatitis;

conditions of the gastrointestinal tract including Crohn's disease, atrophic gastritis, gastritis varialoforme, ulcerative colitis, coeliac disease, regional ileitis, peptic ulceration, irritable bowel syndrome, damage to the gastrointestinal tract resulting from infections by, for example, *Helicobacter pylori*, or from treatments with non-steroidal anti-inflammatory drugs;

and other conditions associated with inflammation.

The compounds will also be useful in the treatment and alleviation of acute or persistent inflammatory or neuropathic pain or pain of a central origin.

The compounds of formula (I) and their pharmaceutically acceptable salts, enantiomers, racemates and tautomers may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the treatment of vascular complications associated with diabetes and in cotherapy with cytokines, for example TNF or interleukins.

The compounds of formula (I) may also show inhibitory activity against the neuronal isoform of nitric oxide synthase. Thus they may also be useful in the treatment of hypoxia, for example in cases of cardiac arrest and stroke, neurodegenerative disorders including nerve degeneration and/or nerve necrosis in disorders such as hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Korsakoffs disease, imbecility relating to a cerebral vessel disorder, sleeping disorders, schizophrenia, depression, autism, seasonal affective disorder, jet-lag, depression or other symptoms associated with Premenstrual Syndrome (PMS), anxiety and septic shock. Compounds of formula (I) may also be expected to show activity in the prevention and reversal of tolerance to opiates and diazepines, treatment of drug addiction, treatment of migraine and other vascular headaches, neurogenic inflammation, in the treatment of gastrointestinal motility disorders, cancer and in the induction of labour.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt, enantiomer, racemate or tautomer thereof.

There is also provided a process for the preparation of such a pharmaceutical composition which comprises mixing the ingredients. The compounds of formula (I), and pharmaceutically acceptable derivatives thereof, may also be advantageously used in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

PREPARATION 1

2-Amidino-3-aminopyridine hydrochloride (a) 3-Azido-2-cyanopyridine

A solution of 3-bromo-2-cyanopyridine (Chem. Pharm. Bull, 1985, 33, 565) (2.6 g, 14.2 mmol) and sodium azide (1.0 g, 15.3 mmol) in DMF (30 ml) was heated at 90° C. for 16 h. The resulting mixture was cooled, water was added and the whole was extracted with ethyl acetate. The combined extracts were washed with saturated brine and dried over magnesium sulphate. Evaporation of the solvent gave the product as an oil, which was purified by flash column chromatography on silica gel, eluting with ethyl acetate/ petrol (1:3 to 1:1) as eluent to afford the product. MS (EI) $^m$/z 145; $^1$H NMR ($d_6$-DMSO) 8.50 (1H, d), 8.09 (1H, d), 7.77 (1H, dd).

(b) 3-Amino-2-cyanopyridine

A solution of 3-azido-2-cyanopyridine (1.44 g, 9.9 mmol) in ethanol (100 ml) was hydrogenated over palladium on carbon (10%, 50 mg) at room temperature and 3.5 p.s.i for 18 h. The catalyst was filtered off over Celite and the filtrate was concentrated to leave the product (1.16 g). $^1$H NMR ($d_6$-DMSO) 7.87 (1H, d), 7.33 (1H, dd), 7.22 (1H, d), 6.28 (2H, s).

(c) 3-Amino-2-(amino(hydroxyimino)methyl)pyridine

A suspension of 3-amino-2-cyanopyridine (1.18 g, 9.9 mmol), sodium methoxide (0.64 g, 12 mmol) and hydroxylamine hydrochloride (0.83 g, 12 mmol) in ethanol (10 ml) was heated under reflux for 1 h. The mixture was filtered and the filtrate concentrated to an oil, which was purified by flash column chromatography on silica gel, eluting with dichloromethane/methanol (50:1 to 10:1) as eluent to afford the product as a yellow solid (0.82 g), MS (+CI) $^m$/z 153 [M+H]$^+$; $^1$H NMR ($d_6$-DMSO) 9.80 (1H, br. s), 7.80 (1H, dd), 7.10 (1H, d), 7.08 (1H, d), 6.62 (2H, s), 5.90 (1H, s).

(d) 2-Amidino-3-aminopyridine hydrochloride

A suspension of 3-amino-2-(amino(hydroxyimino) methyl)pyridine (0.82 g, 5.4 mmol) and wet Raney nickel (ca. 0.1 g) in ethanol (200 ml) was stirred under 3 atmospheres of hydrogen at 60° C. for 16 h. The catalyst was removed by filtration and the solvent evaporated to give the product as an oil, which was dissolved in a small amount of ethanol. Hydrogen chloride in ether (1N, 11 ml) was added with stirring and the precipitate was collected by filtration to give a solid. MS (+CI) $^m$/z 137 [M+H]$^+$, $^1$H NMR ($d_6$-DMSO) 9.15 (4H, br. s), 7.93 (1H, dd), 7.34 (1H, d), 7.26 (1H, d).

PREPARATION 2

4-Amidino-3-aminopyridine hydrochloride (a) 3,5-Dichloro-4-formylpyridine n-Butyllithium (1.6M in hexanes, 9.3 ml, 14.9 mmol) was added dropwise at 0° C. to a solution of diisopropylamine (1.95 ml, 14.9 mmol) in THF (30 ml). After 15 min. at 0° C., the solution was cooled to −78° C. and 3,5-dichloropyridine (2.0 g, 13.5 mmol) was added. After 1 h, methyl formate (0.92 ml) was added and the mixture warmed to room temperature over 2 h, diluted with 1N hydrochloric acid and extracted twice with ethyl acetate. The extracts were washed with brine, dried over sodium sulphate and evaporated to give a yellow oil which solidified, m.p. 110–111° C.

(b) 3.5-Chloro-4-cyanopyridine

A suspension of 3,5-dichloro-4formylpyridine (1.0 g, 5.68 mmol) and hydroxylamine-O-sulphonic acid (0.96 g, 8.5 mmol) in water (20 ml) was heated at 70° C. for 16 h, then cooled and extracted twice with ethyl acetate. The extracts were washed with brine and dried over sodium sulphate. Evaporation of the solvent gave the product as an oil, which was purified by flash column chromatography on silica gel, eluting with dichloromethane/methanol (10:1) to afford the product. MS (+EI) $^m$/z 172/174/176; $^1$H NMR (CDCl$_3$) 8.69 (2H, s).

(c) 5-Azido-3-chloro-4-cyanopyridine

This compound was prepared from 3,5-chloro-4-cyanopyridine following the method of Preparation 1(a) to give a solid. MS (+EI) $^m$/z 151 (M$^+$−N$_2$); $^1$H NMR (CDCl$_3$) 8.89 (1H, s), 8.69 (1H, s).

(d) 5-Amino3-chloro-4-cyanopyridine

Tin (II) chloride (1.42 g, 7.5 mmol) was added to a solution of 5-azido-3-chloro-4-cyanopyridine (0.9 g, 5 mmol) in ethanol (20 ml) and water (0.3 ml). Bubbling ensued. The mixture was stirred for 1 h. and then extracted twice with ethyl acetate. The extracts were washed twice with saturated aqueous sodium bicarbonate and dried over sodium sulphate. Evaporation of the solvent gave the product as an oil, which was purified by flash column chromatography on silica gel, eluting with dichloromethane/ metahnol (10:1) to afford the product. MS (+CI) $^m$/z 152 [M−H]$^+$; $^1$H NMR (d$_6$-DMSO) 8.15 (1H, s), 7.87 (1H, s), 6.88 (2H, s).

(e) 4-Amidino-3-aminopyridine hydrochloride

This compound was prepared from 5-amino-3-chloro-4-cyanopyridine following the method of Preparation 1, steps (c) and (d) to give a solid. MS (+CI) $^m$/z 171 [M+H]$^+$; $^1$H NMR (d$_6$-DMSO) 9.54 (2H, s), 9.34 (2H, s), 8.27 (1H, s), 8.00 (2H, s), 7.55 (2H, d).

PREPARATION 3

3-Amidino-4-aminopyridine hydrochloride (a) 4-Amino-3-cyanopyridine

This compound was prepared from 4-amino-3-formylpyridine following the method of Preparation 2(b) to give the product as a white solid. MS (+EI) $^m$/z 119 (M)$^+$; $^1$H NMR (d$_6$-DMSO) 8.38 (1H, s), 8.12 (1H, d), 7.02 (2H, s), 6.66 (1H, d).

(b) 3-Amidino-4-aminopyridine To ammonium chloride (430 mg, 8.1 mmol) in toluene was added trimethylaluminium (2M in hexane, 4 ml, 8.1 mmol) at 5° C. and the mixture was stirred at room temperature for 2 h. 4-Amino-3-cyanopyridine (320 mg, 2.7 mmol) was added and the reaction mixture was heated at 80° C. overnight. The mixture was cooled, poured onto alumina in chloroform, quenched with ethanol and filtered. The filtrate was concentrated and triturated with ether to give a solid. MS (+EI) $^m$/z 119 (M−NH3)$^+$.

EXAMPLE 1

7-Amino-4,5-dihydro-5-phenylthieno[3,2-d] pyrimidine hydrochloride (a) 3-Aminothiophene-2-thiocarboxamide A solution of 3-aminothiophene-2-carboxamide (4.5 g, 31 mmol) in tetrahydrofuran was treated with Lawesson's Reagent (7.7 g, 190 mmol) and the solution was stirred at room temperature for 18 h. The solvent was removed and the residue purified by chromatography on silica gel using dichloromethane as eluent. The product was obtained as a yellow powder (2.8 g, 56%), m.p. 98–99° C.

(b) 4,5-Dihydro-7-(methylthio)-5-phenylthieno[3,2-d] pyrimidine hydroiodide

A solution of 3-aminothiophene-2-thiocarboxamide (1.0 g, 6.3 mmol), methyl iodide (0.39 ml, 6.3 mmol) and benzaldehyde (0.67 g, 6.3 mmol) in acetonitrile was stirred at room temperature for 18 h. The product was collected by filtration, washed with acetonitrile, then ether and dried (1.58 g, 64%), m.p.193–194° C.

(c) 4,5-Dihydro-7-amino-5-phenylthieno[3,2-d]pyrimidine hydrochloride

A solution of 4,5-dihydro-7-(methylthio)-5-phenylthieno [3,2-d]pyrimidine hydroiodide (0.5 g, 1.29 mmol) in acetonitrile was saturated with dry ammonia gas and then heated at reflux for 20 h. The solvent was removed and the residue triturated with an ether/ethanol mixture to give the hydroiodide salt (92 mg) as a hygroscopic powder, m.p. 179–181° C. This material was converted into the hydrochloride salt (m.p. 229–231° C.) by neutralisation followed by treatment with excess hydrogen chloride in ether.

EXAMPLE 2

Following a process analogous to that of Example 1, the following compounds were prepared:

(a) 5-Cyclopropyl-4,5-dihydro-7-aminothieno[3,2-d] pyrimidine hydrochloride, m.p. 195–196° C.

(b) 5-Ethyl-4,5-dihydro-7-aminothieno[3,2-d]pyrimidine hydroiodide, m.p. 177° C.

(c) 5-(2-Thiazolyl)-4,5-dihydro-7-aminothieno[3,2-d] pyrimidine hydroiodide trihydrate, m.p. 194–195° C.

(d) 5-(2-Furyl)-4,5-dihydro-7-aminothieno[3,2-d] pyrimidine hydroiodide trihydrate, m.p. 239–240° C.

EXAMPLE 3

7-Amino-4,5-dihydro-5-ethynylthieno[3,2-d] pyrimidine hydrochloride (a) Following a process analogous to that of Example 1, the following compound was prepared:

7-Amino-4,5-dihydro-5-(2-(trimethylsilyl)ethnyl) thieno[3,2-d]pyrimidine hydroiodide, MS $^m$/z 250 [M+H]$^+$.

(b) 7-Amino-4,5-dihydro-5-ethynylthieno[3,2-d]pyrimidine hydrochloride

A solution of the product of step (a) (0.47 g, 1.9 mmol) in tetrahydrofuran was treated with tetrabutylammonium fluoride (1 M in THF, 2.27 ml, 2.27 mmol). The solution was stirred at room temperature for 18 h and the solvent was removed under reduced pressure. The residue was purified by chromatography on aluminium oxide (Brockman Grade 1, neutral) using dichloromethane/metahnol mixtures and the crude product fraction was further purified by preparative reverse-phase hplc. The product fractions were concentrated and treated with excess hydrogen chloride in ether to precipitate the hydrochloride salt. After trituration with ether the title compound hydrochloride salt was obtained as a cream powder (14.2 mg), m.p. 19–196° C.

EXAMPLE 4

Ethyl 7'-aminospiro[piperidine-4,5'-(4'H)-(thieno-[3, 2-d]pyrimidine)]-1-carboxylate hydroiodide (a) Ethyl 7'-(methylthio)spiro[piperidine-4,5'-(4'H)-(thieno- [3,2-d]pyrimidine)]-1-carboxylate hydroiodide A solution of 3-aminothiophene-2-thiocarboxamide (0.5 g, 3.16 mmol), methyl iodide (0.2 ml, 3.16 mmol) and N-carbethoxy-4-piperidone (0.47 ml, 3.16 mmol) in acetonitrile was stirred at room temperature for 18 h. The product was collected by filtration, washed with acetonitrile and dried to leave a bright yellow solid (0.88 g), MS (FAB) $^m$/z 326 [M+H]$^+$.

(b) Ethyl 7'-aminospiro[piperidine-4,5'-(4'H)-(thieno-[3,2-d]pyrimidine)]-1-carboxylate hydroiodide A mixture of the product of Example 4(a) (0.88 g, 1.94 mmol) and ammonium iodide (0.28 g, 1.94 mmol) in a minimum volume of acetonitrile was saturated with dry ammonia gas and then heated at reflux for 6h. The solvent was evaporated and the residue purified by chromatography on neutral alumina eluting with dichloromethane/metahnol mixtures, to give, after trituration with ether, the product, as a lemon-coloured powder (0.15 g), m.p. 239° C. (softens at 143° C.).

EXAMPLE 5

Ethyl 4'-amino-3'-chlorospiro[piperidine-4,6'(7'H)-thieno[2,3-d]pyrimidine]-1-carboxylate hydrochloride.

(a) 3-Amidino-2-amino-4-chlorothiophene hydrochloride

Trimethylaluminium (2.0M in toluene, 8.33 mmol, 4.2 ml) was added dropwise to a stirred solution of ammonium chloride (446 mg, 8.33 mmol) in toluene (10 ml) at 5° C. After 2 h at room temperature, 2-amino-4-chloro-3-cyanothiophene (440 mg, 2.78 mmol) was added portionwise over 10 min. and the solution heated to 80° C. for 2 h, cooled, poured onto silica (2 g), and the mixture treated with methanol (10 ml) with stirring. After 5 min. the mixture was filtered, the solid washed with methanol, and the filtrate evaporated to give the crude product as a brown solid (640 mg), MS (+CI) $^m$/z 176 [M+H]$^+$, 300 MHz $^1$H NMR (d$_6$-DMSO) 9.07 (1H, br.s), 8.95 (1H, br.s), 6.92 (1H, br.s), 6.57 (1H, s) (also signals for excess ammonium chloride).
(b) Ethyl 4'-amino-3'-chlorospiro[piperidine-4,6'(7'H)-thieno[2,3-d]pyrimidine]-1-carboxylate hydrochloride.

3-Amidino-2-amino-4-chlorothiophene hydrochloride (130 mg) was heated with N-carboethoxy-4-piperidone (0.6 mmol, 0.1 ml) at 90° C. for 2 h, cooled and evaporated. The residue was purified by flash column chromatography on neutral alumina eluting with dichloromethane/methanol mixtures, and the product was treated with 1N hydrogen chloride in diethyl ether to afford a beige solid, MS (+CI) $^m$/z 329 [M+H]$^+$, $^1$H NMR (d$_6$-DMSO) 6.34 (1H, s), 4.10 (2H, q, J 7.2 Hz), 3.79–3.64 (4H, m), 2.09–1.99 (4H, m) 1.24 (3H, t, J 7.2 Hz).

EXAMPLE 6

4'-Amino-(4-cyanobenzoyl)-spiro[piperidine-4,2'-[1'H]-(pyrido[3,2-d]pyrimidine)]hydrochloride A solution of 2-amidino-3-aminopyridine hydrochloride (0.22 g, 1.05 mmol), 1-(4-cyanobenzoyl)-4-piperidone ethylene ketal (1.08 g, 3.98 mmol) in 1M hydrogen chloride in ether (3 ml) and ethanol (15 ml) was stirred at 70° C. for 18 h. The mixture was cooled, concentrated and purified by flash column chromatography on neutral alumina, eluting with dichloromethane/methanol (10:1 to 5:1) as eluent to afford the product as a yellow solid, m.p. 173–175° C.

EXAMPLE 7

4'-Amino-(2-thienoyl)-spiro[piperidine-4,2'-[1'H]-(pyrido[3,2-d]pyrimidine)]hydrochloride This compound was prepared from 2-amidino-3-aminopyridine hydrochloride following the method of Example 6, to give a yellow solid, m.p. 144–145° C.

EXAMPLE 8

Ethyl 4'-aminospiro[piperidine-4,2'-[1']-(pyrido-[3,2-d]pyrimidine)]-1-carboxylate hydrochloride This compound was prepared from 2-amidino-3-aminopyridine hydrochloride following the method of Example 6, to give a yellow solid, m.p. 135–136° C.

EXAMPLE 9

4'-Amino-(4-cyanobenzoyl)-spiro[piperidine-4,2'-[1'H]-(pyrido-[3,4-d]pyrimidine)]hydrochloride This compound was prepared from 4-amidino-3-aminopyridine hydrochloride following the method of Example 6 to give a yellow solid. MS (+CI) $^m$/z 347 [M+H]$^+$; $^1$H NMR (d$_6$-DMSO) 10.76 (1H, s), 9.66 (1H, s), 8.96 (1H, s), 8.42 (1H, s), 8.15 (1H, s), 8.06 (1H, d), 7.96 (2H, d), 7.81 (1H, d), 7.60 (2H, d), 3.75–3.95 (2H, m), 3.35–3.6 (2H, m), 1.8–2.2 (4H,m).

EXAMPLE 10

Ethyl 4'-aminospiro[piperidine-4,2'[1'H]-(pyrido-[3,4-d]-pyrimidine)]-1-carboxylate hydrochloride This compound was prepared from 4amidino-3-aminopyridine hydrochloride following the method of Example 6, to give a yellow solid MS (+CI) $^m$/z 290 [M+H]$^+$; $^1$H NMR (d$_6$-DMSO) 8.24 (1H, s), 7.95 (1H, d), 7.60 (1H, s), 7.50 (1H, s), 4.04 (2H, q), 3.4–3.6 (4H, m), 1.6–1.9 (4H, m), 1.19 (3H, t).

EXAMPLE 11

4'-Amino-(4-cyanobenzoyl)-spiro[piperidine-4,2'-[1'H]-(pyrido-[4,3-d]pyrimidine)]hydrochloride A suspension of 3-amidino-4-aminopyridine (0.56 g), 1-(4-cyanobenzoyl)-4-piperidone ethylene ketal (1.08 g, 3.98 mmol) and potassium carbonate (0.5 g) in ethanol (20 ml) was stirred at 70° C. for 48 h. The mixture was cooled, concentrated and purified by flash column chromatography on neutral alumina, eluting with dichloromethane/metahnol (20:1 to 1:1) to afford the product as a white solid. MS (+CI) $^m$/z 347 [M+H]$^+$; $^1$H NMR (d$_6$-DMSO) 8.99 (1H, s), 8.34 (1H, d), 7.97 (2H, d), 7.60 (2H, d), 7.01 (1H, d), 3.3–4.0 (4H,m), 1.8–2.2 (4H, m).

EXAMPLE 12

Ethyl 4'-aminospiro[piperidine-4,2'-[(1'H]-(pyrido[2,3-d]pyrimidine)]-1-carboxylate hydrochloride (a) Ethyl 3',4'-dihydro-4'-oxospiro[piperidine-4,2'-[1'H]-(pyrido[2,3-d]pyrimidine)]-1-carboxylate 3-Amido-2-aminopyridine (0.5 g, 3.6 mmol), N-carbethoxy-4-piperidone (0.7 g, 4.02 mmol) and 3A molecular sieves (4 g) in 1M hydrogen chloride in ether (3 ml) and ethanol (10 ml) were heated at reflux for 1 h. The mixture was absorbed onto silica gel and purified by flash column chromatography on silica gel, eluting with dichloromethane/methanol (20:1 to 5:1) to afford the product as a white solid (0.8 g). MS (+CI) $^m$/z 291 [M+H]$^+$; $^1$H NMR (d$_6$-DMSO) 8.56 (1H, s), 8.36 (1H, s), 8.21 (1H, d), 8.02 (1H, d), 6.80 (1H, dd), 4.04 (2H, q), 3.4–3.62 (4H, m), 1.65–1.92 (4H, m), 1.18 (3H, t).
(b) Ethyl 3',4-dihydro-4'-thioxospiro[piperidine-4,2'-[1'H]-(pyrido[2,3-d]pyrimidine)]-1-carboxylate A solution of ethyl 3',4'-dihydro-4'-oxospiro[piperidine-4,2'-[1'H]-(pyrido[2,3-d]-pyrimidine)]-1-carboxylate (0.74 g, 2.55 mmol) and Lawesson's reagent (0.62 g, 1.5 mmol) in dioxane (15 ml) was heated at reflux for 2 h. The mixture was absorbed onto silica gel and purified by flash column chromatography on silica gel, eluting with dichloromethane/methanol (50:1) to afford the product as a white solid (0.7 g). MS (+CI) $^m$/Z 307 [M+H]$^+$; $^1$H NMR (d$_6$-DMSO) 10.37 (1H, dd), 8.34 (1H, dd), 8.24 (1H, dd), 8.10 (H, s), 6.76 (1H, dd), 4.04 (2H, q), 3.6–3.78 (2H, m), 3.3–3.5 (2H, m), 1.75–1.90 (4H, m), 1.21 (3H, t).
(c) Ethyl 4'-aminospiro[piperidine-4,2'-[1'H]-(pyrido-[3,4-d]pyrimidine)]-1-carboxylate hydrochloride To a solution of ethyl 3',4-dihydro-4'-thioxospiro [piperidine-4,2'-[1'H]-(pyrido[2,3-d]-pyrimidine)]-1-carboxylate (0.5 g, 1.63 mmol) in acetonitrile (20 ml) at room temperature was added iodomethane (0.1 ml, 1.63 mmol). The solution was stirred for 20 h, evaporated and purified by flash column chromatography on silica gel, eluting with dichloromethane/methanol (10:1) as eluent to afford the thioimidate. The thioimidate was dissolved in acetonitrile saturated with ammonia (20 ml) and heated at 150° C. in a bomb for 48 h. The solution was evaporated and the residue was purified by flash column chromatography on neutral alumina, eluting with dichloromethane/methanol (10:1) to afford, after being acidified with 1M hydrogen chloride in ether, the product. MS (+CI) $^m$/z 290 [M+H]$^+$; $^1$H NMR (d$_6$-DMSO) 10.34 (1H, s), 9.40 (1H, s), 8.61 (1H, s), 8.41 (1H, s), 8.40 (1H, dd), 8.26 (1H, dd), 6.89 (1H, dd), 4.05 (2H, q), 3.4–3.7 (4H, m), 1.85–2.01 (1H, m), 1.20 (3H, t).

EXAMPLE 13

4-Amino-2-(2-thienyl)-pyrido[3,2-d]pyrimidine hydrochloride

A solution of 2-amidino-3-amninopyridine hydrochloride (0.10 g, 0.47 mmol) and 2-thiophenealdehyde (60 mg, 0.54 mmol) in ethanol (1 ml) was stirred at 50° C. for 18 h. The mixture was cooled, then concentrated and the residue was purified by flash column chromatography on neutral alumina, eluting with dichloromethane/methanol (20:1 to 10:1) as eluent to afford the product as a brown/red solid, m.p. 186–187° C.

EXAMPLE 14

7'-Amino-1-(6-cyano-3-pyridinecarbonyl)spiro [piperidine-4,5'-(4'H)-(thieno[3,2-d]-pyrimidine)] hydroiodide This was prepared by the method of Example 4 using 1-(6-cyano-3-pyridinecarbonyl)-4-piperidone ethylene ketal (WO 97/14686). M.p. 260–261° C. (dec.).

Screens

The pharmacological activity of compounds according to the invention was tested in the following screens.

Screen 1

The activity of compounds of formula (I), or a pharmaceutically acceptable salt, enantiomer or tautomer thereof, may be screened for nitric oxide synthetase inhibiting activity by a procedure based on that of Förstermann et al., Eur. J. Pharm., 1992, 225, 161–165. Nitric oxide synthase converts $^3$H-L-arginine into 3H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM L-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% $CO_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsir inhibitor (10 mg/ml), aprotinin (5 mg/ml) and phenylmethylsulphonyl fluoride (50 mg/ml).

For the assay, 25 $\mu$l of substrate cocktail (50 mM Tris-HCl (pH 7.5 at 20° C.), 400 $\mu$M NADPH, 20 $\mu$M flavin adenine dinucleotide, 20 $\mu$M flavin mononucleotide, 4 $\mu$M tetrahydrobiopterin, 12 $\mu$M L-arginine and 0.025 mCi L-[$^3$H] arginine) is added to wells of a 96 well filter plate (0.45 $\mu$M pore size) containing 25 $\mu$l of a solution of test compound in 50 mM Tris-HCl The reaction is started by adding 50 $\mu$l of cell lysate (prepared as above) and after incubation for 1 hour at room temperature is terminated by addition of 50 $\mu$l of an aqueous solution of 3 mM nitroarginine and 21 mM EDTA.

Labelled L-citrulline is separated from labelled L-arginine using Dowex AG-50W. 150 $\mu$l of a 25% aqueous slurry of Dowex 50W (Na$^+$ form) is added to the assay after which the whole is filtered into 96 well plates. 75 $\mu$l of filtrate is sampled and added to wells of 96 well plates containing solid scintillant. After allowing the samples to dry the L-citrulline is quantified by scintillation counting.

In a typical experiment basal activity is 300 dpm per 75 $\mu$l sample which is increased to 1900 dpm in the reagent controls. Compound activity is expressed as $IC_{50}$ (the concentration of drug substance which gives 50% enzyme inhibition in the assay) and aminoguanidine, which gives an $IC_{50}$ (50% inhibitory concentration) of 10 $\mu$M, is tested as a standard to verify the procedure. Compounds are tested at a range of concentrations and from the inhibitions obtained $IC_{50}$ values are calculated. Compounds that inhibit the enzyme by at least 25% at 100 $\mu$M are classed as being active and are subjected to at least one retest.

In the above screen, the compounds of Examples 1 to 14 were tested and gave $IC_{50}$ values of less than 25 $\mu$M indicating that they are expected to show useful therapeutic activity.

Screen 2

Compounds also show activity against the human form of induced nitric oxide synthase as can be demonstrated in the following assay.

Enzyme is prepared, after induction, from the cultured human colon adrenocarcinoma cell line DLD1 (obtained from the European Collection of Animal Cell Culture—cell line number 90102540). DLD1 cells are cultured in RPMI 1640 medium supplemented with 10% foetal bovine serum, 4 mM L-glutamine and antibiotics (100 units/ml penicillin G, 100 $\mu$g/ml streptomycin and 0.25 $\mu$g/ml amphotericin B). Cells are routinely grown in 225 cm$^3$ flasks containing 35 ml medium kept at 37° C. and in a humified atmosphere containing 5% $CO_2$.

Nitric oxide synthase is produced by cells in response to interferon-$\gamma$ (IFN-$\gamma$) and interleukin-1$\beta$ (IL-1$\beta$). The medium from confluent flasks is removed and replaced with 25 ml (per flask) of fresh medium containing 250 units/ml IL-1$\beta$ and 1000 units/ml IFN-$\gamma$. After a period of 17–20 hours in culture, harvesting of cells is accomplished by scraping the cell monolayer from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X100, 0.1 mM dithiothreitol and a cocktail of protease inhibitors including leupeptin (2 $\mu$g/ml), soya bean trypsin inhibitor (10 $\mu$g/ml), aprotonin (5 $\mu$g/ml) and phenylmethylsulphonyl fluoride (50 $\mu$g/ml).

For the assay, 25 $\mu$l of substrate cocktail (50 mM Tris-HCl (pH 7.5), 400 $\mu$M NADPH, 20 $\mu$M flavin adenine dinucleotide, 20 $\mu$M flavin mononucleotide and 4 $\mu$M tetrahydrobiopterin) is added to the wells of a 96-well plate. Test compounds are preincubated with enzyme by adding together with 40 $\mu$l of cell lysate (prepared as above) and incubating for 1 hour at 37° C. at the end of which period 10 $\mu$l of 30 $\mu$M L-arginine and 0.025 $\mu$Ci of L-[$^3$H]-arginine in 50 mM Tris-HCl is added to start the enzymatic reaction.

Incubation is continued for a further 1 hour at 37° C. The reaction is terminated by addition of 50 μl of an aqueous solution of 3 mM nitroarginine and 21 mM EDTA.

Labelled L-citrulline is separated from labelled L-arginine using Dowex AG-50W. 120 μl of a 25% aqueous slurry of Dowex 50W is added to 96 well filter plates (0.45 μm pore size). To this is added 120 μl of terminated assay mix. 75 μl of filtrate is sampled and added to the wells of 96 well plates containing solid scintillant. After allowing the samples to dry the L-citrulline is quantified by scintillation counting.

In a typical experiment basal activity is 300 dpm per 75 μl sample of reagent controls, which is increased to 3000 dpm in the presence of enzyme. Compound activity is expressed as $IC_{50}$ (the concentration of drug substance which gives 50% enzyme inhibition in the assay) and L-NMMA, which gives an $IC_{50}$ of about 0.4 μM is tested as a standard to verify the procedure. Compounds are tested at a range of concentrations and from the inhibitions obtained $IC_{50}$ values are calculated.

In this screen the compounds of Examples 1 to 14 give $IC_{50}$ values less than 25 μM, indicating that they are predicted to show useful therapeutic activity.

What is claimed is:

1. A compound of formula (1)

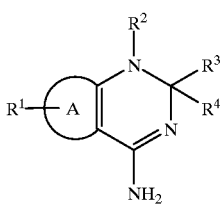

(I)

wherein
$R^1$ represents hydrogen, alkyl C1 to 6, alkoxy C1 to 6, halogen or trifluoromethyl;
$R^2$ hydrogen or alkyl C1 to 6;
A represents a thienyl ring;
  (i) $R^3$ represents phenyl, a six membered heterocyclic aromatic ring containing 1 to 3 nitrogen atoms, or a five membered heterocyclic aromatic ring containing 1 to 3 heteroatoms which may be the same or different and are selected from O, N and S, which phenyl or heterocyclic aromatic ring may be optionally substituted by alkyl C1 to 6, alkenyl C2 to 6, alkynyl C2 to 6, alkoxy C1 to 6, halogen, hydroxy, alkylthio C1 to 6, cyano, trifluoromethyl, nitro or a group —$NR^5R^6$;
  and $R^4$, $R^5$ and $R^6$ independently represent hydrogen or alkyl C1 to 6; or
  (ii) $R^3$ represents alkyl C1 to 8, alkenyl C2 to 8 or alkynyl C2 to 8; and $R^4$ represents hydrogen or alkyl C1 to 6; or
  (iii) $R^3$ and $R^4$ together represent $(CH_2)_a.Z.(CH_2)_b$, Z representing $N(COOR^7)$,
  wherein $R^7$ represents alkyl C1 to 6 or haloalkyl C1 to 6, or $R^7$ represents a group $(CH_2)_nYR^9$ wherein n represents an integer from 2 to 5, Y represents O, S or a bond and
  $R^9$ represents alkyl C1 to 6 optionally substituted by halogen or nitro, or $R^9$ represents phenyl optionally substituted by alkyl C1 to 6, halogen or nitro; and
  a and b independently represent an integer 1 to 3, provided that a+b is 3 or 4; or
  (iv) $R^3$ and $R^4$ together represent $(CH_2)_a.Z.(CH_2)_b$, Z representing $N(COR^8)$, wherein $R^8$ represents phenyl, a six membered heterocyclic aromatic ring containing 1 to 3 nitrogen atoms or a five membered heterocyclic aromatic ring containing 1 to 3 heteroatoms which may be the same or different and are selected from O, N and S, which phenyl or heterocyclic aromatic ring may be optionally substituted by alkyl C1 to 6, alkoxy C1 to 6, halogen, nitro, cyano, trifluoromethyl, alkylsulphonyl C1 to 6 or aminosulphonyl; and
a and b independently represent an integer 1 to 3, provided that a+b is 3 or 4; or a pharmaceutically acceptable salt, enantiomer, racemate or tautomer thereof.

2. A compound of formula (I), according to claim 1 wherein the compound is a thieno[2,3-d]pyrimidine or a thieno[3,2-d]pyrimidine derivative.

3. A compound of formula (I), according to claim 1 wherein $R^3$ represents phenyl, cyclopropyl, ethyl, thiazolyl, ethynyl or furanyl.

4. A compound of formula (I), according to claim 1, wherein $R^3$ and $R^4$ are in accordance with option (iii) in claim 1, Z represents $N(COOC_2H_5)$, and a and b each has a value of 2.

5. A compound of formula (I) which is:
7-amino-4,5-dihydro-5-phenylthieno[3,2-d]pyrimidine;
5-cyclopropyl-4,5-dihydro-7-aminothieno[3,2-d]pyrimidine;
5-ethyl-4,5-dihydro-7-aminothieno[3,2-d]pyrimidine;
5-(2-thiazolyl)-4,5-dihydro-7-aminothieno[3,2-d]pyrimidine;
5-(2-furyl)-4,5-dihydro-7-aminothieno[3,2-d]pyrimidine;
7-amino-4,5-dihydro-5-ethynylthieno[3,2-d]pyrimidine;
ethyl 7'-aminospiro[piperidine-4,5'(4'H)-thieno[3,2-d]pyrimidine]-1-carboxylate;
ethyl 4-amino-3'-chlorospiro[piperidine-4,6'(7'H)-thieno[2,3-d]pyrimidine]-1-carboxylate;
or a pharmaceutically acceptable salt, enantiomer or tautomer thereof.

6. A pharmaceutical composition comprising a compound of formula (I) according to claim 1, or a pharmaceutically acceptable salt, enantiomer or tautomer thereof, in admixture with a pharmaceutically acceptable adjuvant, diluent or carrier.

7. A method of treating, or reducing the risk of, human diseases or conditions in which inhibition of nitric oxide synthase activity is beneficial which comprises administering a therapeutically effective amount of a compound of formula (I), as defined in claim 1, or a pharmaceutically acceptable salt, enantiomer or tautomer thereof, to a person suffering from, or at increased risk of, such diseases or conditions.

8. A method of treatment according to claim 7 in which it is predominantly inducible nitric oxide synthase that is inhibited.

9. A method of treating, or reducing the risk of, inflammatory disease in a person suffering from, or at risk of, said disease, wherein the method comprises administering to the person a therapeutically effective amount of a compound of formula (I), as defined in claim 1, or a pharmaceutically acceptable salt, enantiomer or tautomer thereof.

10. The method of treatment as claimed in claim 9 wherein the disease is asthma or rheumatoid arthritis.

11. A method of treating, or reducing the risk of, pain in a person suffering from, or at risk of, said condition, wherein the method comprises administering to the person a therapeutically effective amount of a compound of formula (I), as defined in claim 1, or a pharmaceutically acceptable salt, enantiomer or tautomer thereof.

12. A method of treating, or reducing the risk of, inflammatory disease in a person suffering from, or at risk of, said disease, wherein the method comprises administering to the person a therapeutically effective amount of a combination of a compound of formula (I), as defined in claim 1, or a pharmaceutically acceptable salt, enantiomer or tautomer thereof, with a COX-2 inhibitor.

13. A process for the preparation of the compound of formula (I), as defined in claim 1, or a pharmaceutically acceptable salt, enantiomer or tautomer thereof, wherein the process comprises:

(a) reaction of a compound of formula (II)

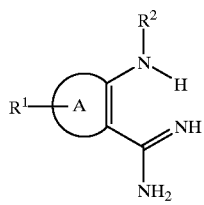

(II)

wherein A, $R^1$ and $R^2$ are as defined above, with a compound of formula (III) or an acetal derivative thereof $$R^3 \, C \, O \, R^4 \quad (III)$$

wherein $R^3$ and $R^4$ are as defined above; or (b) reaction of a compound of formula (IV) or (IV')

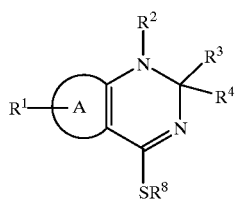

(IV)

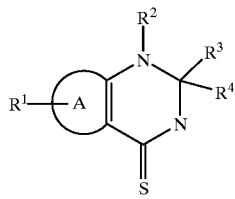

(IV')

wherein A, $R^1$, $R^2$, $R^3$ and $R^4$ are as defined above, and $R^8$ represents an alkyl group; with ammonia or an equivalent thereof; or (c) preparation of a compound of formula (I) in which $R^3$ and $R^4$ are according to option (i) in the general definition of formula (I) given above and one or both of $R^5$ and $R^6$ represents alkyl C1 to 6, by alkylation of a corresponding compound in which one or both of $R^5$ or $R^6$ represents hydrogen; or (d) preparation of a compound of formula (I) in which $R^2$ represents alkyl C1 to 6, by alkylation of a corresponding compound in which $R^2$ represents hydrogen; or (e) deprotection of a compound of formula (I) in which one or more nitrogen atoms and/or another atom is protected; or (f) preparation of a compound of formula (I) in which $R^3$ and $R^4$ are in accordance with option (iv) in the general definition of formula (I) given above, by reacting a compound of formula (V)

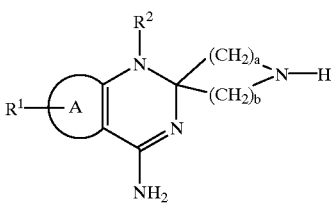

(V)

wherein A, $R^1$, $R^2$, a and b are as defined above, with a compound of formula (VI)

$$X—L \quad (VI)$$

wherein X represents $COOR^7$ or $COR^8$, $R^7$ and $R^8$ being as above, and L is a leaving group;

and where desired or necessary converting the resultant compound of formula (I), or another salt thereof, into a pharmaceutically acceptable salt thereof, or vice versa, and where desired converting the resultant compound of formula (I) into an optical isomer thereof.

* * * * *